United States Patent [19]
Phillips et al.

[11] Patent Number: 5,928,189
[45] Date of Patent: Jul. 27, 1999

[54] ACTIVITY RESPONSIVE THERAPEUTIC DELIVERY SYSTEM

[76] Inventors: Robert E. Phillips, 4 Country Glen Rd., Fallbrook, Calif. 92028; Ben A. Otsap, 7661 Airport Blvd., Los Angeles, Calif. 90045

[21] Appl. No.: 08/844,822

[22] Filed: Apr. 22, 1997

[51] Int. Cl.[6] .................................................. A61M 31/00
[52] U.S. Cl. ............................................................. 604/65
[58] Field of Search .................................. 604/65, 66, 67, 604/30, 31, 32–34, 49, 50, 53, 246, 247, 248, 249; 128/DIG. 12, DIG. 13

*Primary Examiner*—Manuel Mendez
*Attorney, Agent, or Firm*—Allen A. Dicke, Jr.

[57] ABSTRACT

One or more physical activity sensors, such as pressure switches, position sensors and accelerometers, as well as a breath sensor are connected to control a valve. The valve is electrically actuated and has first and second states. A control circuit between the sensors and the valve increase actuation of the valve when continuing activity is sensed. The valve has a single coil and is bistable so that it does not require continuous energization in either state. The fluid is preferably respiratory oxygen so that more oxygen is delivered when the person is active.

37 Claims, 5 Drawing Sheets

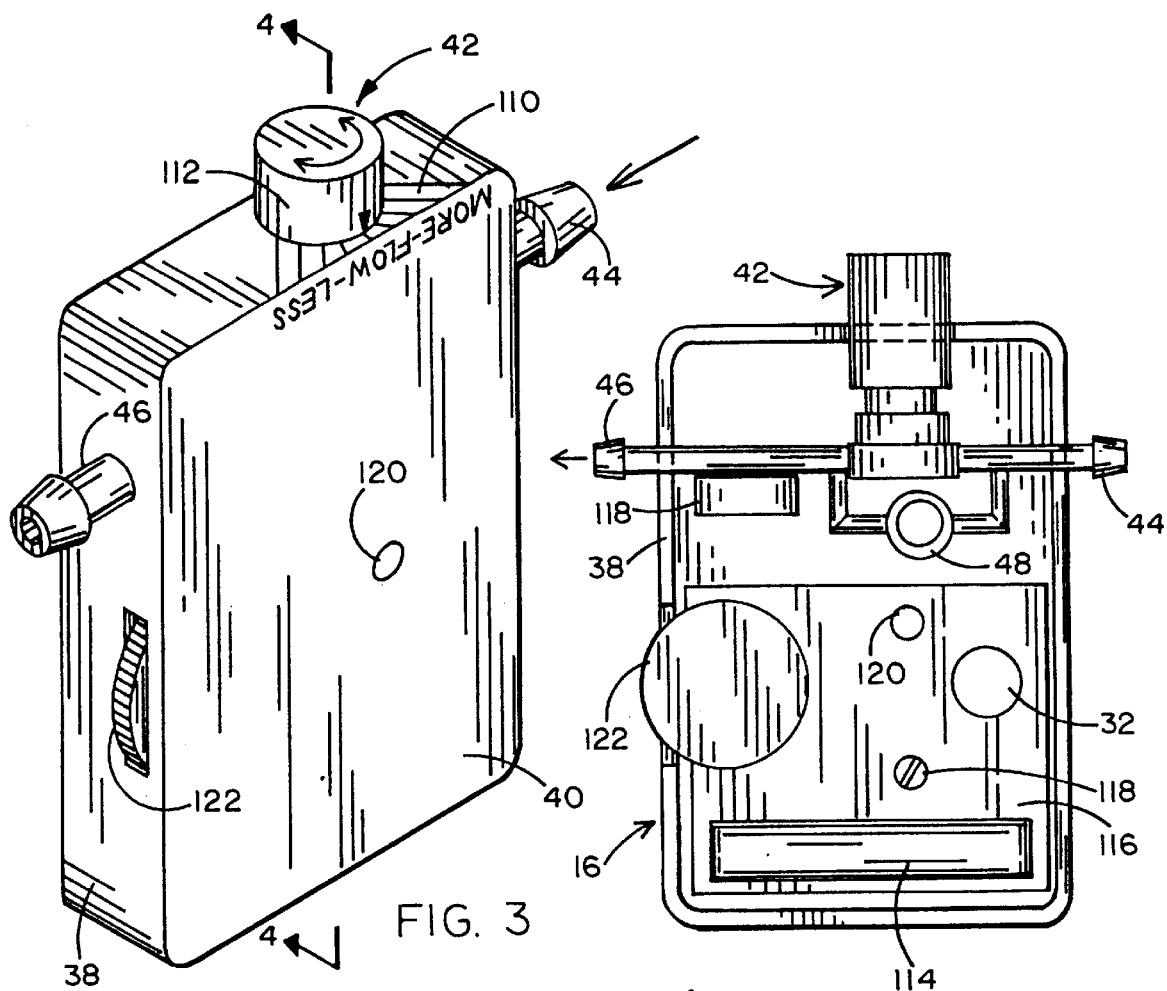
FIG. 3
FIG. 4
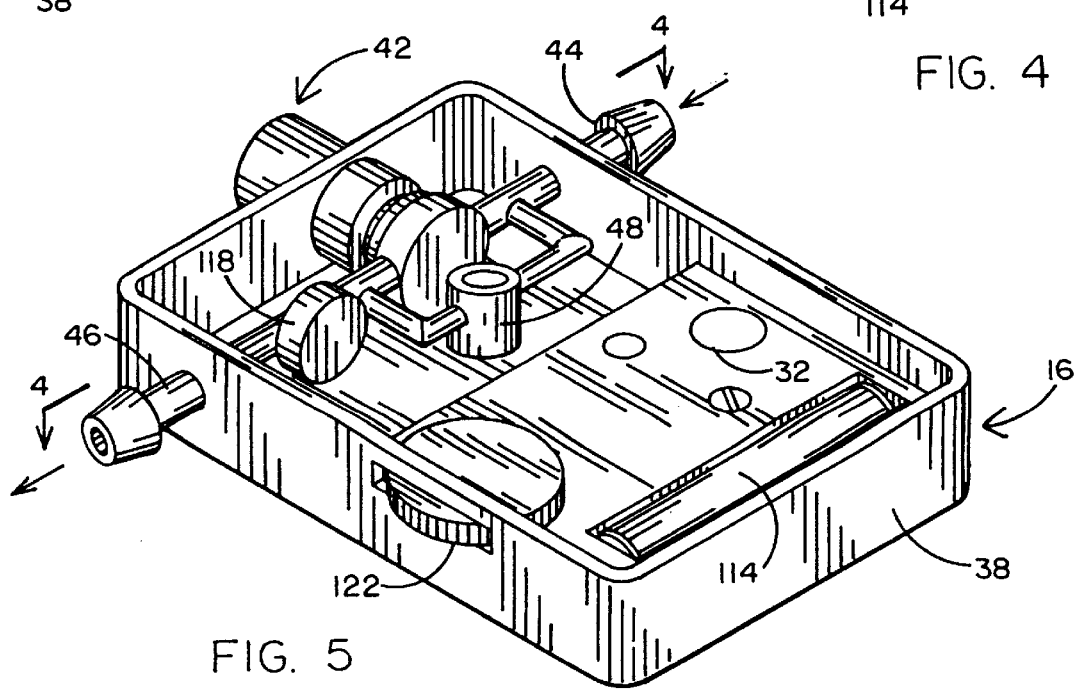
FIG. 5

ACTIVITY RESPONSIVE THERAPEUTIC DELIVERY SYSTEM

FIELD OF THE INVENTION

This invention is directed to a system for intervening in human bodily processes, usually therapeutically in response to the activity of the person. A particular example of such intervention is delivering oxygen to a person in need of supplemental oxygen in response to changes in the level of his physical activity.

BACKGROUND OF THE INVENTION

Intervention in bodily processes is often required to aid or control the body for one reason or another. Such intervention may be therapeutic in the sense of administering fluids for improvement in body condition. One widely employed intervention is the delivery of oxygen to a person to aid in his breathing.

In the past, it has been common to deliver oxygen to a person needing such therapy by enclosing the nose and mouth of the individual needing such treatment with a "tent." Oxygen is supplied to the interior of the tent so that the person inhales an oxygen enriched gas. A nasal cannula has been utilized to avoid the tent, but for patients confined to bed, the supply of oxygen to the cannula was also at a fixed rate. The supply of oxygen in such structures was regulated to be substantially constant.

It is usual for a patient to tell his doctor that "I feel fine sitting around and watching TV, but when I get up and start walking, I get out of breath." The physician then makes pulmonary function tests and determines that the individual needs supplemental oxygen. The outcome of these initial tests are variable, depending on the individual, and it is frequently determined that the individual needs one liter a minute of supplemental oxygen while sedentary. However, to be on the safe side, the physician will typically write a prescription for two liters a minute in order to make sure that the patient receives adequate oxygen when he is active. As used in this application, "supplemental" means in addition to that supplied naturally in the ambient air. One reason an excess of oxygen is prescribed is because there is a known limit on the rate of increase of heart rate in response to decrease in blood oxygen. This means that an increase in activity causes a decrease in blood oxygen and this causes an increase in heart rate, but that increase in heart rate is limited. Respiratory rate is substantially proportional to heart rate and thus breathing rate sensitive oxygen additions are not fully responsive to the need for blood oxygen.

It is not good therapeutic practice to prescribe more oxygen than the patient needs. It is desirable to prescribe the proper amount, and utilize a delivery system, such as disclosed herein for increasing the supply when the patient needs more oxygen. Normally, conservation is not important because the supply is large and inexpensive. However, when the patient is ambulatory and is receiving his oxygen from a small pressure bottle, or is otherwise on a limited oxygen supply, conservation is desirable. In accordance with an additional and optional structure, the system also has a breath sensor so that oxygen is only delivered upon inhalation and the number of inhalations between oxygen supply pulses is a function of sensed activity. In accordance with this invention, the therapeutic delivery system is sensitive to physical activity by the patient and increases the supply of fluid for medical intervention, which is oxygen in accordance with the preferred embodiment disclosed herein.

SUMMARY OF THE INVENTION

In order to aid in the understanding of this invention, it can be stated in essentially summary form that it is directed to an activity responsive system which acts to supply fluid to a patient for intervention in his bodily processes, which in accordance with a preferred embodiment of the system is a delivery system wherein the activity of a person requiring oxygen therapy is sensed and oxygen is delivered in accordance with the sensed activity. Sensing of activity is by body position or body motion and the amount of supplemental oxygen may be increased from zero or a predetermined low level to a higher level as required by the person's increased metabolism as a result of his increased activity. The supplemental oxygen is preferably delivered by an electrical pulse actuated valve which does not require electric power to maintain it in either its open or its closed state to thereby conserve battery power.

It is thus a purpose and advantage of this invention to sense activity of a patient and intervene differently in the patient's bodily processes as a result of detecting the activity. One preferred example is changing the dose of a fluid administered to the body in accordance with the amount of detected activity.

It is thus another purpose and advantage of this invention to create an activity responsive oxygen delivery system which detects physical activity of a person receiving oxygen therapy and, in accordance with one mode of operation, providing a supply of oxygen to the person without reference to his heart rate or his respiratory rate.

It is another purpose and advantage of this invention to provide an oxygen delivery system which has one or more pressure, position or acceleration sensors to control a valve which delivers additional oxygen to the patient.

It is another purpose and advantage of this invention to provide an oxygen delivery system which has a breath sensor which is active when oxygen conservation is desired. The breath sensor opens the oxygen supply valve only during inhalation. Activity sensing controls the fraction of inhalations which will receive the oxygen pulse.

It is a further purpose and advantage of this invention to provide an oxygen delivery system wherein an oxygen valve having a single coil is energized with an electric pulse of a first polarity to open and is retained in the open position by the magnetic properties of the valve and is subsequently electrically pulsed with a pulse of a second polarity to close wherein it is retained in the closed position without the utilization of electric power to thus preserve battery current.

Further purposes and advantages of this invention will become apparent from a study of the following portion of this specification, the claims and the attached drawings.

BRIEF DESCRIPTION OF THE DRAWINGS

FIG. 3 is an isometric view of the oxygen control unit.

FIG. 4 is a plan view of the oxygen control unit with parts taken in section, as seen generally along line 4—4 of FIG. 3.

FIG. 5 is a similar view, as seen in an isometric projection.

DESCRIPTION OF THE PREFERRED EMBODIMENT

In broad terms, this invention is directed to intervention in bodily processes and a modification of the intervention as a result of physical activity of the person being treated. The intervention may be therapeutic and the intervention may be transdermal. The intervention may be by electro stimulation. Another manner in which intervention may be achieved is through a needle-created port for the delivering of medication or other intervention material. In its most preferred embodiment, the therapeutic process is directed to the delivering of gaseous oxygen to a patient through a nasal cannula or the like.

In the delivery of oxygen, the intent is to deliver sufficient oxygen, but not too much because too much oxygen also as deleterious effects. The proper amount of supplemental oxygen must be delivered to the person when he is inactive. This is oxygen which is supplemental to that normally received from the ambient air due to respiration. Some persons need no supplemental oxygen during inactive periods and thus the rate of supply of supplemental oxygen may be zero. An active person requires more oxygen. It is desirable to determine that the person has become active and as a result of this determination provide a predetermined rate of flow of supplemental oxygen. This will always be above zero flow.

The principle objective of any oxygen delivery system is to deliver sufficient oxygen but not excessive oxygen. Oxygen conservation is not normally a consideration because normally there is a sufficient oxygen supply available. In hospital and similar environments, the piped oxygen supply often comes from the boiling off of a liquid oxygen supply. In home environments, the source is often an oxygen concentrator. In either case, conservation is not important. However, for ambulatory patients who move a greater distance than a hose length from their concentrator, a high-pressure oxygen bottle is employed. The amount of oxygen is necessarily limited because the pressure bottle is small enough to be portable. On those occasions, conservation of oxygen delivered to the patient has importance. The detailed description which follows describes the delivery of supplemental oxygen as a preferred example of intervention in bodily processes, and particularly therapeutic processes.

Figures 1, 2:
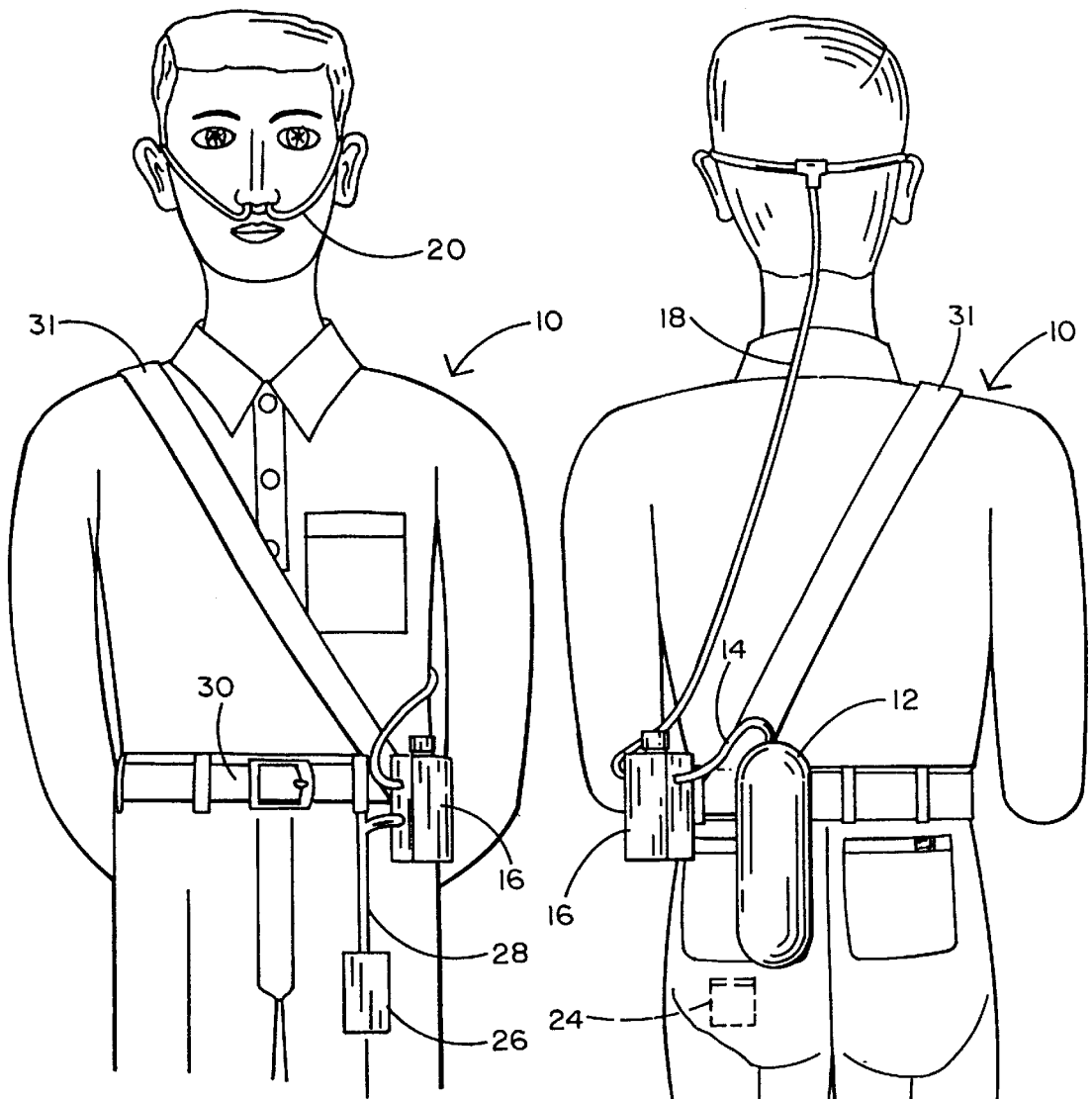
FIG. 1 is a front elevation view of a male patient utilizing the activity responsive oxygen delivery system of this invention, with parts of the drawing broken away.
FIG. 2 is a rear view thereof, with one foot raised.

FIGS. 1 and 2 show a person 10 who requires supplemental oxygen. The source may be a liquid oxygen tank or an oxygen concentrator. When away from such a large source, the person may carry with him an oxygen source 12 which is shown to be a pressurized oxygen bottle. The source may be a small pressurized bottle carried on the person or a larger pressurized bottle carried on a dolly. The source 12 has its own pressure reduction system and delivers oxygen through tube 14 to control unit 16. The control unit 16 regulates the flow of oxygen, as is described below, and the oxygen from the control unit is delivered through tube 18 to nasal cannula 20.

It is the regulation of oxygen flow by the control unit 16 to which this invention is directed. It is the activity of the person 10 which provides input signals to control the amount of flow. Activity sensors of various types can be provided. As is shown in FIG. 2, foot switch 22 indicates when the person 10 is in the standing position, as compared to the sedentary position. Switch 24 is positioned in the clothing of the person 10 and is positioned at his buttocks so that switch 24 is actuated when the person 10 is seated. Therefore, it is called a "seat switch." As seen in FIG. 1, switch 26 hangs pendulously from the person's belt at the front of his thigh. The thigh switch 26 is supported by a strap 28 from his belt 30. The thigh switch 26 is positioned pendulously to indicate one mode when the person is standing as shown in FIG. 1. The other mode is when the person is seated and the thigh switch is raised to a more horizontal position. A mercury switch would be suitable for such use. The seat switch and foot switch are pressure sensitive switches. Any other pressure or position sensing switch can be employed as generally indicated by sensor 27 seen in FIG. 6.

In accordance with the preferred embodiment, the oxygen bottle 12 and control unit 16 are carried on the person's torso supported by a shoulder strap 31 or harness. Furthermore, it can be carried on the person's belt 30 for convenience.

The foot switch 22, seat switch 24, thigh switch 26, and sensor switch 27 are examples of activity responsive sensors. In addition, an accelerometer 32 is positioned within control unit 16 as shown in FIGS. 4 and 5. These sensors, including the accelerometer 32, each provide a signal representing activity of the person 10, as compared to inactivity. The accelerometer is a piezo accelerometer and its output signal is low. Therefore, its output is connected through piezo amplifier 34 to sensor signal line 36, see FIG. 6. Each of the sensors is connected to signal line 36. It is understood that these sensors are representative of sensors sensing activity of the person 10. One or more of the sensors can be employed.

Figure 7:
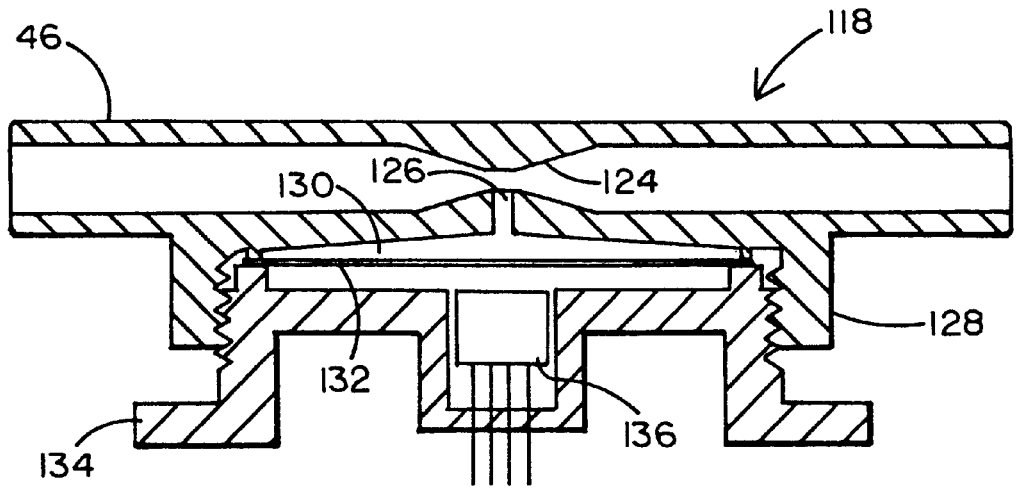
FIG. 7 is a longitudinal section through a breath sensor, for detecting inhalations.
Figure 8:
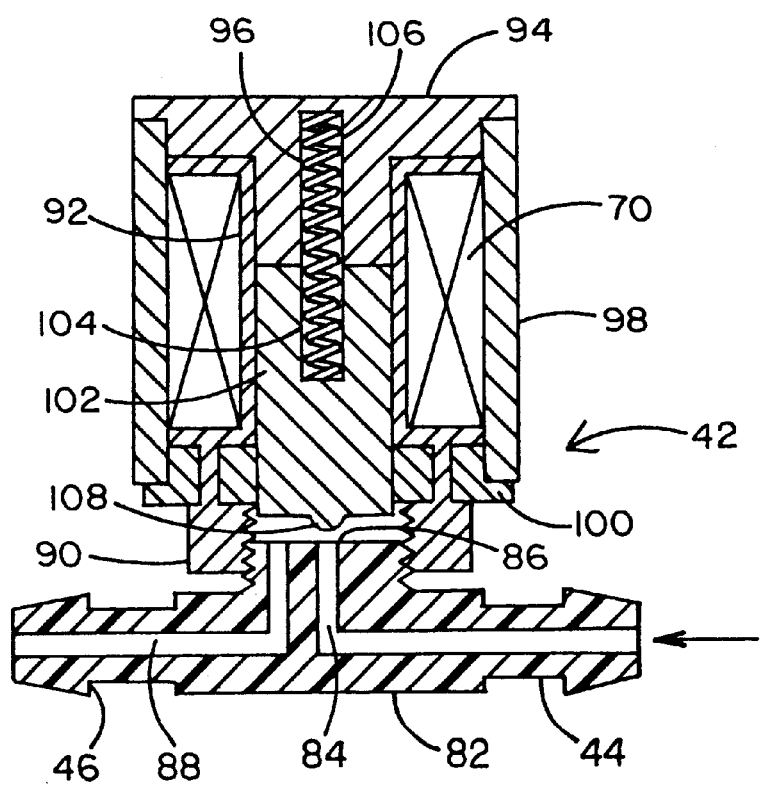
FIG. 8 is a central section through the oxygen control valve shown in the retained, open position.

Referring to FIGS. 3, 4, and 5, control unit 16 has a housing 38 and cover 40. The cover is shown removed in FIGS. 4 and 5. Valve 42 is mounted within the housing and its solenoid may extend from the housing, as shown in FIGS. 3, 4 and 5. The valve will be explained in more detail with respect to FIGS. 7, 8 and 9. Valve 42 has an inlet 44 and an outlet 46 which are preferably barbed for respective attachment of tubes 14 and 18.

It is a principal purpose of this invention to provide a system which provides a low level of flow during inactivity and a higher level of flow during activity of the person being treated. It is understood that the low-flow state may be zero flow or may be a predetermined lower flow rate such as one liter per minute (STP). In order to provide a minimum flow, when the valve 42 is closed, bypass needle valve 48 is provided. As seen in FIGS. 4 and 5, the bypass needle valve 48 is connected in parallel to the valve 42 in order to permit a predetermined amount of flow from inlet 44 to outlet 46, even when the valve 42 is closed. The needle valve configuration of valve 48 is arranged so that the valve is adjustable from a zero flow to another higher predetermined flow, as required by the inactive person.

The valve 42 is especially designed and constructed with a single coil so that a short current pulse of one polarity through the coil opens the valve and it remains open without further energization. A short current pulse in the opposite polarity through the single coil closes the valve without further energization. Thus, valve 42 is a special valve because it is stable in either the on or off position, without requiring electric power. It thus conserves battery power. The configuration of valve 42 is described below.

Figure 6:
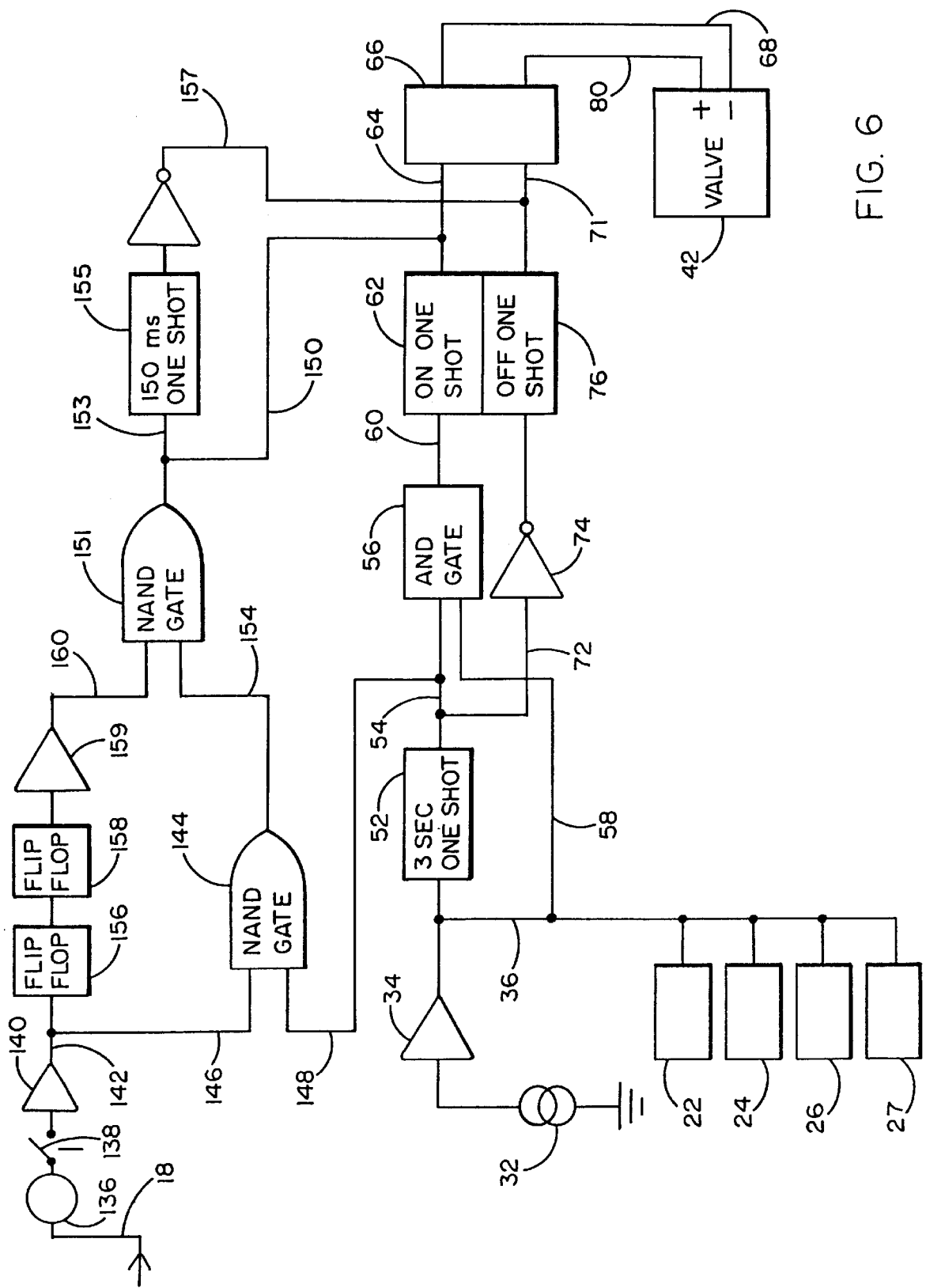
FIG. 6 is a schematic electrical circuit for detecting patient activity and controlling the oxygen valve.

The control circuit 50 is schematically shown in FIG. 6. A signal is produced in line 36 when any one of the sensors is actuated. This actuates circuit 52 which is a one-shot multi vibrator circuit which turns on the output in line 54 after a short delay for a predetermined time. In the present case, the preferred time is three seconds. Line 54 is one of the inputs to AND gate 56.

Signal line 36 is also connected by line 58 to the AND gate. This circuit works in a manner that the first signal in line 36 is transferred on line 58 to AND gate 56. At the same time, the signal in line 36 energizes the input through three-second one-shot circuit 52. After a slight delay, sufficient to permit the signal in line 58 to disappear if it is a mere electronic pulse, the three-second one-shot circuit 52 energizes line 54 to produce a three-second long signal in line 54. If a second signal is produced in line 36, it goes to the AND gate 56 through line 58. If the second signal comes along within the three seconds before the time out of one-shot circuit 52, then the AND gate 56 is turned on. The purpose of this arrangement is to prevent a single short pulse in line 36 from providing a signal in line 60. The resulting signal in line 60 is delivered out of the AND gate. One-shot circuit 62 provides an output pulse in line 64 when line 60 is first actuated. The declining output in the three-second one-shot circuit 52 at the end of its three-second timeout is also conveyed in line 72 to inverter 74, as discussed below.

H-gate 66 is an electronic version of a double-throw double-pole switch. The H-gate 66 is provided with power and is connected so that when line 64 provides a signal to the H-gate, lines 68 and 80 are energized with a predetermined pulse in one polarity and when input signal line 71 provides a signal pulse, the H-gate 66 is connected to provide the opposite polarity to lines 68 and 80. Lines 68 and 80 are connected to the valve coil 70. The coil 70 is schematically shown in valve 42 in FIGS. 7 and 8. The on one-shot circuit 62 provides a pulse in line 64 of proper length. This pulse is sufficient to open the valve and condition the magnetic properties of the valve hold it open.

As long as the person 10 provides an activity signal at least once in each three-second interval defined by the timing circuit 52, the timing circuit 52 does not time out. This means that it continuously energizes line 54. In the case where there is not a second activity signal in line 36, then the falling signal in line 54 is connected through line 72 to inverter 74. This falling signal produces an inverter output signal to the "off" one-shot circuit 76 which produces an off pulse in line 71. The signal in line 71 switches the H-gate 66 with a properly conditioned pulse as to pulse length. The "off" one-shot 76 produces this pulse and delivers it through line 71 and through H-gate 66 to the coil 70 in the opposite polarity. This pulse releases the magnetic latching of the valve 42.

The valve 42 is a special valve. It is a latching solenoid valve which employs a single actuating coil 70 to perform both the opening and closing of the valve without utilizing a mechanical latch or without requiring that the coil remain energized during one of the valve states. A residual magnetic force holds the valve open and a return spring is used to close the valve when the magnetic latching force holding the valve open is overcome. This latching valve utilizes the properties of the magnetic material itself to provide the latching force. The valve body 82 carries the barbed inlet 44 and outlet 46 connections. Interiorly, the valve body has a central inlet passage 84 which terminates in seat 86. The body is preferably made of synthetic polymer composition material and the seat is preferably integral therewith. Outlet passage 88 extends from the top of the body from a position beside the inlet passage. The upper portion of the body has external threads.

Collar 90 has internal threads which are engaged on the threads on the body. The coil 70 is wound on non-metallic bobbin 92 which is integrally molded of synthetic polymer composition material with the collar 90. Lower pole piece 100 has a plurality of axial holes therethrough which permit the bobbin and collar to be molded together. This molding together decreases the number of joints to reduce the possibility of leakage. Upper pole piece 94 covers the upper end of the bobbin 92 and extends part way down the hollow interior thereof. The upper pole piece has a spring pocket 96 therein. The upper flange of the upper pole piece extends outward and has a step for receiving tubular shell 98. The lower pole piece 100 is received in the lower end of the shell and carries collar 90. The plunger 102 slides within the bore of bobbin 92 and lower pole piece 100.

Plunger 102 also has a spring pocket 104 therein. Compression spring 106 is housed in the spring pockets 96 and 104. The plunger 102 has a valve disk 108 on its nose and this valve disk mates with valve seat 86 when the plunger 102 is in its lowered position. In this position, spring 106 has sufficient force to overcome the pressure of oxygen in passage 84 times the area of the passage. This is the condition shown in FIG. 8, and in that condition the valve is closed. The plunger, shell, upper pole piece and lower pole piece are all made from a special solenoid grade stainless steel which resists oxygen corrosion.

Figure 9:
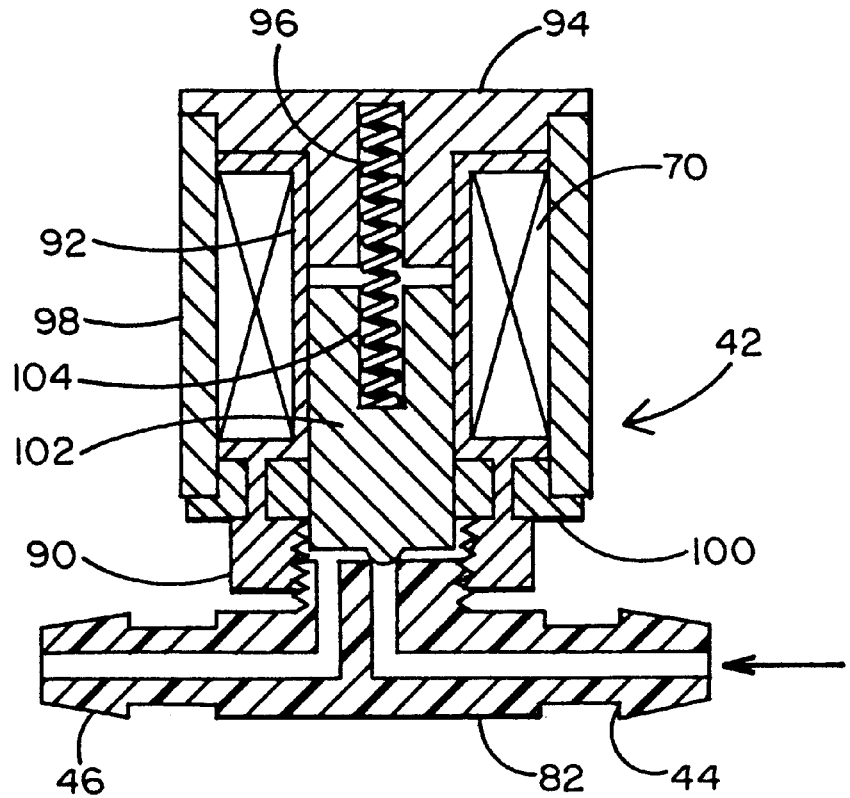
FIG. 9 is a similar view showing the valve in the closed position.

The valve is normally closed as shown in the FIG. 9 position. The coil 70 in valve 42 is connected as shown in FIG. 6. When a short current pulse is applied to the coil 70, it produces a magnetic attraction between the upper pole piece and the plunger. This causes the plunger to rise to close the gap between the plunger and the upper pole piece. This opens the valve to the position shown in FIG. 8. When the short electrical signal is terminated, the residual magnetic flux present in the magnetic circuit provides sufficient magnetic attraction between the plunger and the upper pole piece to retain the plunger in the upper, open position against the force of spring 106.

When it is desired to close the valve, an electrical signal of reverse polarity is applied to the coil 70. This signal is of sufficient magnitude and duration to release the magnetic retention of the plunger. The spring moves the plunger to the lowered position shown in FIG. 8. The closing pulse must be sufficient to release the plunger, but must not be too strong or too long or the valve "close" signal will actually reverse the magnetic field in the entire structure and retain the plunger in the open position. Thus, the release pulse must be carefully controlled. This is accomplished by the one-shot circuit 76 and H-gate which produce signals of the proper polarity, duration and level. The magnetic stainless steel is preferably a martensitic stainless steel which is annealed to maximize the magnetic properties. In the particular valve design, it was found that the minimum saturation flux density must be 14,200 Gausses and the residual flux density must be at least 6,000 Gausses. When the material is fully annealed, it exhibits a coercive force of 1.5 to 2.5 Oersted from an applied magnetic field of 10,000 Gausses.

The valve 42 is capable of remaining in the open position and in the closed position without the application of current. Furthermore, the change in state between the open and closed position requires only a small amount of current. This is very effective in limiting the valve current requirements and thus is very effective in extending battery life. It has been disclosed how bypass needle valve 48 provides a minimum oxygen flow when the valve 42 is closed.

Figure 10:
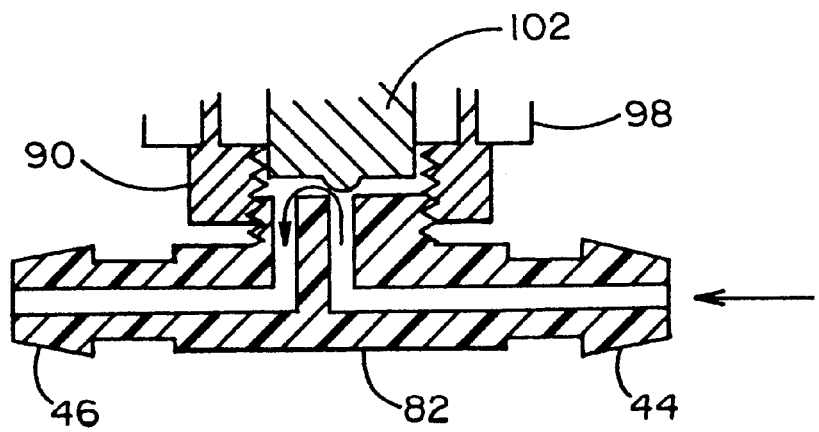
FIG. 10 is a similar view, with parts broken away, showing the valve adjusted so as to provide a minimal flow even in the closed position.

As an alternative construction to providing that bypass valve, the valve 42 can be adjusted so that it provides the desired minimum flow in the "closed" position. This is the position shown on FIG. 10. It is seen that the entire solenoid portion in collar 90 of the valve 42 can be unscrewed away from valve body 82. This reduces the force of the spring 106 toward valve closure. By carefully unscrewing the solenoid portion in collar 90 from the valve body, the seat force decreases until a selected minimum flow is achieved in the "closed" position. It is for this reason that the solenoid portion of the valve 42 extends out of the case, as shown in FIGS. 3, 4, and 5. FIG. 3 shows indicia 110 and witness line 112 which permit the person 10 to adjust the minimum flow as desired. This mode of operation is considered less preferred than the utilization of the bypass needle valve 48 because the bypass needle valve 48 can be more accurately adjusted to achieve the desired minimum flow value.

The control unit 16 is self-contained in the sense that it provides its own power from battery 114. The circuit card 116 carries all of the electronics shown in FIG. 6, except the sensor switches and the valve itself. The circuit card also carries a sensitivity adjustment screw 118 for adjusting the time of one-shot 52 which is maintained on for the predetermined time, in this case, 3 seconds. The LED 120 indicates the fact that the circuit is operative. Thumb wheel 122 is accessible from the exterior of the case, as shown in FIGS. 3, 4, and 5 and adjusts the sensitivity of accelerometer 32.

For operation in the breath sensing mode, the outlet tube 46 carries breath sensor 118, as seen in FIGS. 3 and 5. The breath sensor 118 is shown in cross-sectional detail in FIG. 7. In the breath sensor 118 the outlet tube 46 carries a restricted neck 124 which forms a venturi. Venturi port 126 leads away from the throat of the venturi to transfer pressure signals. Sensor body 128 has a chamber 130 therein which is in communication with port 126. Chamber 130 is closed by flexible diaphragm 132 which is clamped in place by cap 134. The cap 134 may be screwed in place as indicated. The space below the diaphragm may be vented or not depending on the size of the lower chamber and the desired sensitivity, which is also related to the diaphragm flexibility.

When the patient 10 inhales, he reduces pressure in the cannula which is connected to outlet tube 46. This reduction in pressure travels as a wave front and is quickly sensed at the venturi. The increased flow reduces the pressure in chamber 130 which is above diaphragm 132. A combination pair of light-emitting diode and light-sensing diode are placed in diode package 136. Diode package 136 is fitted into a recess in the cap and positioned so that the light-emitting diode and light-sensing diode face the diaphragm 132. Upon flexing of the diaphragm, the light-sensing diode sees the change in reflection from the diaphragm and emits a signal. Thus, intake of breath is sensed.

The diode package 136 is the transducer that converts the pressure wave signal representing the beginning of breath intake to an electrical signal. FIG. 6 shows how the signal from sensor 136 is connected to operate valve 42. The principle of this portion of the circuit is to open the valve 42 for a predetermined length of time in a smaller fraction of a predetermined number of breaths when the person 10 is inactive, and a larger fraction of a predetermined number of breaths when the person is active. When it is desired to deliver oxygen in accordance with sensed breath intake, the switch 138 is closed. The breath signal is amplified in the amplifier 140 so that the inspiration signal is delivered in line 142. Line 142 is connected to NAND gate 144 through line 146. NAND gate 144 also has the input through line 148 from line 54. NAND gates have a high output except when both inputs are high. Line 54 is energized for 3 seconds after activity is sensed. Thus, when activity is sensed and breath inspiration is sensed, line 154 carries a low signal to NAND gate 151.

Line 142 is also connected to flip-flop 156 which in turn is connected to flip-flop 158. The output of flip-flop 158 is connected to inverter 159 and then to line 160 which is the other input of NAND gate 151. With one or both input lines 154 and 160 to NAND gate 151 low, the gate puts a high signal in line 153. This signal in line 150 turns on valve 42. After a 150 millisecond delay, delay timer 155 energizes line 157 which is connected to line 71. This turns off the valve 42 after it has been open for 150 milliseconds. This 150 millisecond open time is sufficient to provide an oxygen pulse during inspiration.

NAND gates 144 and 151 are gates which function such that the output is high except when both inputs are high. Output 153 is connected to turn the valve on and to the input of 150 millisecond delay timer 155. The function of flip-flops 156 and 158 is to act as a one-in-four divider so that for every inspiration pulse in line 142, each fourth inspiration pulse is present in line 160. When output 153 is high, after a 150 millisecond delay, delay timer 155 energizes line 157 which is connected to line 71. This turns off the valve 42 after it has been open for 150 milliseconds. This 150 millisecond open time is sufficient to provide an oxygen pulse during inspiration. During inactivity, each fourth inspiration pulse opens valve 42 and during activity, every inspiration pulse opens valve 42. At the same time, delay timer 152 is energized so that after 150 milliseconds, line 157 is energized to close valve 42. In this way, when switch 138 is closed, the person 10 receives an oxygen pulse during every fourth breath, when he is inactive. He receives an oxygen pulse during each breath when he is active.

This invention has been disclosed in its most preferred embodiments. It is clear that it is susceptible to numerous modifications and embodiments without the exercise of the inventive faculty. Accordingly, the scope of this invention is defined by the scope of the following claims.

What is claimed is:

1. An activity responsive intervention system for delivering fluid to a person for his metabolic use, comprising:
    a source of metabolically active fluid,
    means for delivering metabolically active fluid to a person;
    fluid control means connected to both said source of metabolically active fluid and to said means for delivering metabolically active fluid to the person, said fluid control means having valve means therein having a first and a second state, said valve means in said first state being for permitting lower flow of metabolically active fluid therethrough than through said valve means when said valve means is in its second state; and
    activity sensor means positioned to be actuated by the person's body, said activity sensor means being connected to said control means so that when activity is sensed, said valve is moved from its first state to its second state.

2. The activity responsive intervention system of claim 1 wherein said activity sensor means includes an accelerometer connected to said fluid control means to signal when the person's body accelerates.

3. The activity responsive intervention system of claim 1 wherein said activity sensor means is a pressure switch which is configured to be positionable on the person so that the pressure thereon changes from a first state to a second state when the person commences activity.

4. The activity responsive intervention system of claim 1 wherein said activity sensor means comprises a position sensor which is configured to be positionable on the person's body so that when the person moves from an inactive position to an active position said position switch transmits an activity signal to said fluid control means.

5. The activity responsive intervention system of claim 1 wherein said fluid control means has a control circuit therein to receive activity signals and said valve is an electrically actuated valve and said fluid control means has a battery therein for powering said control circuit and actuating said valve.

6. The activity responsive intervention system of claim 1 further including breath sensing means for sensing the inhalation of the metabolically active fluid by the person, said breath sensing means being connected to control said valve and said activity sensor means being connected to increase the amount of metabolically active fluid delivered to the person.

7. The activity responsive intervention system of claim 5 further including breath sensing means for sensing the inhalation of the metabolically active fluid by the person, said breath sensing means being connected to control said valve and said activity sensor means being connected to increase the amount of metabolically active fluid delivered to the person.

8. The activity responsive intervention system of claim 5 wherein said valve is configured so that it can remain in said first state without continuous power consumption and can remain in said second state without continuous power consumption.

9. The activity responsive intervention system of claim 8 wherein said valve has an electromagnetic coil therein and has a magnetic plunger movable in response to energization of said coil, said valve having a spring therein urging said plunger toward its first state so that it remains in its first state until energization, said control circuit providing a pulse to energize said electric coil and magnetically move said plunger so that said valve is in its second, open state, and said valve is configured so that residual magnetism retains said plunger in said second state against the force of said spring until the residual magnetism is released by a pulse in said coil of opposite polarity to said energization pulse.

10. The activity responsive intervention system of claim 9 wherein said control circuit limits the length of the electric pulses to move said plunger between said first and second state.

11. The activity responsive intervention system of claim 10 wherein said activity sensor means includes an accelerometer connected to said fluid control means to signal when the person's body accelerates.

12. The activity responsive intervention system of claim 10 wherein said activity sensor means is a pressure switch which is configured to be positionable on the person so that the pressure thereon changes from a first state to a second state when the person commences activity.

13. The activity responsive intervention system of claim 10 wherein said activity sensor means comprises a position sensor which is configured to be positionable on the person's body so that when the person moves from an inactive position to an active position said position switch transmits an activity signal to said oxygen control means.

14. The activity responsive intervention system of claim 9 wherein said source of metabolically active fluid is a source of respiratory oxygen.

15. The activity responsive intervention system of claim 14 wherein said means for delivering metabolically active fluid to a patient is a nasal cannula.

16. The activity responsive intervention system of claim 15 further including breath sensing means for sensing the inhalation of the metabolically active fluid by the person, said breath sensing means being connected to control said valve and said activity sensor means being connected to increase the amount of metabolically active fluid delivered to the person.

17. A bistable electrically actuated valve comprising:
valve body, a valve seat in said valve body;
a plunger, a valve disk on said plunger, said valve disk being movable from a position where it is on said seat with said plunger in a first position to a second position of said plunger where said valve disk is off of said valve seat;
a pole piece, said plunger and said pole piece being made of magnetic material, said pole piece being configured so that said plunger lies against said pole piece when said plunger is in its second position; and
an electromagnetic coil position adjacent said pole piece and adjacent said plunger, said electromagnetic coil being sized and positioned so that when energized in a first polarity magnetism created by said electromagnetic coil moves said plunger from its first position to its second position where it lies against said pole piece, said plunger and said pole piece being configured and constructed of such material that said plunger is retained in said second position against said pole piece by residual magnetism and without energization of said electromagnetic coil.

18. The bistable valve of claim 17 further including a control circuit connected to said electromagnetic coil, said control circuit being connected to said electromagnetic coil and being configured to produce a pulse in said electromagnetic coil in a first polarity to move said plunger from its first position to its second position and being configured to produce a pulse in a second and opposite polarity to magnetically release said plunger from said pole piece so that said plunger can move from its second position to its first position.

19. The bistable valve of claim 18 further including a spring urging said plunger toward its first position.

20. The bistable valve of claim 19 wherein said pole piece is a first pole piece and there is also a second pole piece, said second pole piece having an opening therethrough through which said plunger is movably positioned and further including a tubular shell around said electromagnetic coil, said shell and said second pole piece also being made of magnetic material.

21. The bistable valve of claim 17 wherein said valve disk is directly mounted on said plunger and said valve seat is adjustably mounted with respect to said plunger so as to permit a desired amount of fluid to flow past said valve seat even when said plunger is in its first position.

22. An activity responsive intervention system comprising:
a source of metabolically active fluid;
a valve connected to said source of metabolically active fluid, said valve having a first position and a second position, said valve passing a lower flow of fluid in its first position than in its second position;
means for delivering metabolically active fluid to a person;
control means for controlling said valve between its first position and its second position, said valve, said means for controlling said valve and said means for delivering fluid to a person all being portable for being carried with the person when he is inactive and when he is active; and means for sensing the beginning of activity by the person, said means for sensing being connected to said valve control means for moving said valve from its first position to its second position when activity is sensed.

23. The activity responsive intervention system of claim 22 wherein said means for sensing is at least one of a group consisting of pressure sensing means, position sensing means and acceleration sensing means, said control means including a timer, said activity sensor being connected to said timer so that when activity is sensed for a timed period, said timer has an output signal, said timer being connected to move said valve to its second position when activity exceeding the timed period is sensed.

24. The activity responsive intervention system of claim 23 wherein said circuit includes means for moving said valve from said second position to said first position when inactivity is sensed for a timed period.

25. The activity responsive intervention system of claim 24 wherein said valve is bistable so that it requires only a pulse to move to its second position and only a pulse to move to its first position.

26. The activity responsive intervention system of claim 25 wherein said circuit comprises a timer connected to a pulse generator to generate a pulse for moving said valve to its second position when activity is sensed and a pulse generator connected to said valve to deliver an opposite pulse to said valve to move said valve to its first position when inactivity is sensed for the timed period.

27. The activity responsive intervention system of claim 22 further included a breath inspiration sensor, said breath inspiration sensor being connected to said control means so that said valve is actuated to its second position on only one of a plurality of sensed breaths when the person is inactive and said means for sensing the beginning of activity being connected to said control means for moving said valve to its second position during a larger fraction of sensed breaths.

28. The activity responsive intervention system of claim 23 wherein said source of metabolically active fluid is a source of respiratory oxygen and said means for delivering metabolically active fluid to a person is a nasal cannula for delivering respiratory oxygen to the person.

29. An activity responsive intervention system comprising:
   a source of metabolically active breathing respiratory fluid;
   a valve connected to said source of metabolically active breathing respiratory fluid, said valve having a first position and a second position, said valve passing a lower flow of fluid in its first position than in its second position;
   means for delivering metabolically active breathing respiratory fluid to a person, sensor means connected to said means for delivering metabolically active respiratory fluid to a person for sensing inspiration of respiratory fluid by the person from said means for delivering metabolically active respiratory fluid;
   control means for controlling said valve between its first position and its second position;
   said valve, said means for controlling said valve and said means for delivering metabolically active respiratory fluid to a person all being portable for being carried with a person when he is inactive and when he is active; and
   means for sensing the beginning of activity by the person, said means for sensing being connected to said valve control means so that said inspiration sensor means causes movement of said valve from its first position to its second position only on a fraction of sensed breaths when the person is inactive and a larger fraction of sensed breaths when the person is active.

30. The activity responsive intervention system of claim 29 wherein said breath sensor comprises a diaphragm connected to said means for delivering metabolically active respiratory fluid to a person so that said diaphragm deflects upon inspiration by the person and there is means for detecting deflections of said diaphragm.

31. The activity responsive intervention system of claim 30 wherein said means for detecting diaphragm deflection is an electro-optical means.

32. The method of supplying a metabolically active respiratory fluid to a patient comprising the steps of:
   placing on the patient a valve, a valve control circuit and means to deliver metabolically active respiratory fluid from said valve to the patient;
   placing on the patient an activity sensor and connecting the activity sensor to control the valve between a first, low-flow state and a second, higher-flow state; and
   connecting a supply of metabolically active respiratory fluid to the valve so that when no activity is sensed, the valve is in its low-flow state and when activity is sensed, the valve is in its high-flow state so that more fluid is applied to the patient when he is active.

33. The method of claim 32 wherein the activity sensor senses at least one of: patient pressure, patient position and patient acceleration.

34. The method of claim 32 wherein the valve is bistable and the control unit emits a signal of a first polarity to move the valve to the higher-flow position and emits a signal of a second polarity to move the valve to its first, low-flow position.

35. The method of claim 34 wherein the low-flow position is a zero flow position.

36. The method of claim 32 wherein the metabolically active respiratory fluid is respiratory oxygen and the means to deliver is a nasal cannula.

37. The method of claim 32 further including:
   connecting an inspiration sensor to the means to deliver metabolically active respiratory fluid to detect inspiration by the fluid; and
   controlling the valve to open only during a smaller fraction of a group of sensed inspiration when the patient is inactive and controlling the valve to be open a larger fraction of the group of sensed inspirations when the patient is active.

* * * * *